(12) United States Patent
Cavazos

(10) Patent No.: US 11,324,627 B2
(45) Date of Patent: May 10, 2022

(54) MALE CONSTRICTOR RING

(71) Applicant: Filiberto Cavazos, Nuevo León (MX)

(72) Inventor: Filiberto Cavazos, Nuevo Leon (MX)

( * ) Notice: Subject to any disclaimer, the term of this patent is extended or adjusted under 35 U.S.C. 154(b) by 0 days.

(21) Appl. No.: 16/765,831

(22) PCT Filed: Nov. 21, 2018

(86) PCT No.: PCT/MX2018/000123
§ 371 (c)(1),
(2) Date: May 20, 2020

(87) PCT Pub. No.: WO2019/103595
PCT Pub. Date: May 31, 2019

(65) Prior Publication Data
US 2020/0289306 A1    Sep. 17, 2020

(30) Foreign Application Priority Data

Nov. 22, 2017  (MX) ............... MX/a/2017/014979

(51) Int. Cl.
A61F 5/41    (2006.01)

(52) U.S. Cl.
CPC ........... A61F 5/41 (2013.01); A61F 2005/411 (2013.01); A61F 2005/414 (2013.01)

(58) Field of Classification Search
CPC .............. A61F 5/41; A61F 2005/411; A61F 2005/414; A61H 19/00; A61H 19/30; A61H 19/32; A61H 19/50
USPC ................................................ 600/38–41
See application file for complete search history.

(56) References Cited

U.S. PATENT DOCUMENTS

| 4,539,980 | A | | 9/1985 | Chaney |
| 5,306,227 | A | | 4/1994 | Osborn et al. |
| 5,526,803 | A | | 6/1996 | Kelly |
| 5,954,631 | A | * | 9/1999 | Gorsuch .................. A61F 5/41 600/41 |
| 6,039,750 | A | * | 3/2000 | Kubalak ............... A61F 2/0054 128/DIG. 25 |
| 6,926,666 | B2 | | 8/2005 | Magee |
| 2002/0033179 | A1 | * | 3/2002 | Burgos ..................... A61F 5/41 128/842 |
| 2014/0179996 | A1 | | 6/2014 | Oh et al. |

FOREIGN PATENT DOCUMENTS

WO    WO 1998/012986 A3    4/1998

OTHER PUBLICATIONS

International Search Report issued in application No. PCT/MX2018/000123, dated Jul. 1, 2019.

* cited by examiner

Primary Examiner — Samuel G Gilbert
(74) Attorney, Agent, or Firm — Knobbe Martens Olson & Bear, LLP

(57) ABSTRACT

A constrictor ring made of a flexible but resistant material adapted to surround the entire base circumference of the penis tightly, acting in this way as a constrictor device that prevents blood from escaping from the penis, thus maintaining the erection, wherein the constrictor ring has an adjuster to adjust the diameter of the ring; a grip that allows the user to firmly push the constrictor ring towards the pubic joint in a precise position and with a sleeve made of a rigid material that surrounds the ring in a position that matches the urethra when the ring is correctly placed, thus protecting the urethra against possible damage when the ring is adjusted.

7 Claims, 2 Drawing Sheets

MALE CONSTRICTOR RING

BACKGROUND OF THE INVENTION

A. Technical Field of the Invention

This invention is related with devices to assist men in maintaining penile erection, and particularly with a constrictor ring made out of a flexible but resilient material adapted to surround the entire circumference of the base of the penis in a tight manner, acting as a constrictor device that prevents blood from escaping from the penis, thus maintaining the erection. The constrictor ring of this invention is characterized by having means to adjust the diameter of the ring and loops located on the periphery of the ring, that allows the user to firmly push the constrictor ring toward the pubis joint (symphysis pubis) in the precise position where the main venous drainage can be obstructed.

B. Description of Background Art

Erectile dysfunction is defined by the Mexican Social Security Institute as the inability to achieve penile rigidity for the time necessary to achieve a satisfactory sexual relationship.

The absence of an erection is due to the fact that the brain does not send the muscles the necessary information to generate a sexual stimulus and consequently the penis does not increase in length or thickness. The causes can be psychological, organic or mixed. In previous art, there are a large number of devices to achieve the rigidity of the penis (achieve an erection), as for example vacuum pumps. However, once the erection of the penis is achieved, it tends to be lost quickly since the blood that fills the cavities of the penis escapes through the main venous drainage, for which there are the so-called constrictor rings that are placed in the penis base in order to exert a pressure on the position where main venous drainage is located, preventing this way blood from escaping from the penis.

There are many designs of constrictor rings, some of which are described in the following documents.

U.S. Pat. No. 3,461,863 discloses a flexible constrictor ring, which has fastening means for adjusting the diameter of the ring and therefore the pressure it exerts, wherein said means frictionally hold the upper portions of the ring. The main disadvantage of this ring is that it is difficult to correctly position it once adjusted, since there is no way to firmly hold the ring to push it firmly towards the base of the penis.

PCT International Patent Application Publication No. WO1998012986A2 discloses a constrictor ring which has clamping means for adjusting the diameter of the ring comprising other engaging elements or projections that lock with internal grooves corresponding internal walls of the ring. Like the ring of U.S. Pat. No. 3,461,863, its main disadvantage is that it is difficult to correctly position it once adjusted, since there is no way to firmly hold the ring to push it firmly towards the base of the penis.

On the other hand, the documents U.S. Pat. Nos. 3,759,253, 4,539,980, 5,306,227 and 6,926,66B2 describe constrictor rings that have rings or fastening handles formed on the periphery of the rings, which allow the user to push them down and to the sides, which allows adjusting the ring firmly against the base of the penis, however they do not have the means to adjust its diameter and therefore the circumferential tension exerted on the base of the penis.

In view of the problems described above, the applicant developed a constrictor ring made of a flexible material that has means to be able to adjust the diameter of the ring and fastening means comprising of loops located on the periphery of the ring that allow the user to push firmly the constrictor ring towards the pubic joint (symphysis pubis) in the precise position where the main venous drainage can be obstructed.

Additionally, the lower portion of the constrictor ring of the present invention has a sleeve made of a rigid material that surrounds the ring in a position that matches the urethra when the ring is position correctly, thus protecting the urethra against possible damage when the ring is adjusted.

SUMMARY OF THE INVENTION

It is therefore the main objective of this invention to provide a constrictor ring made of a flexible material that has means to be adjusted in the diameter of the ring.

It is another main objective of this invention to provide a constrictor ring of the nature described above which additionally has fastening means comprising of loops located on the periphery of the ring that allows the user to firmly push the constrictor ring towards the pubis articulation (symphysis pubis) in the precise position where the main venous drainage can be obstructed.

It is a further objective of this invention to provide a constrictor ring of the above-described nature, which additionally has a sleeve made of a rigid material surrounding the ring in a position that matches the urethra when the ring is correctly placed, thus protecting the urethra against possible damage when the ring is adjusted.

These and other objectives and advantages of the present invention will become apparent to those of ordinary skills in the art from the following detailed description of the invention.

DETAILED DISCLOSURE OF THE INVENTION

Figure 1:
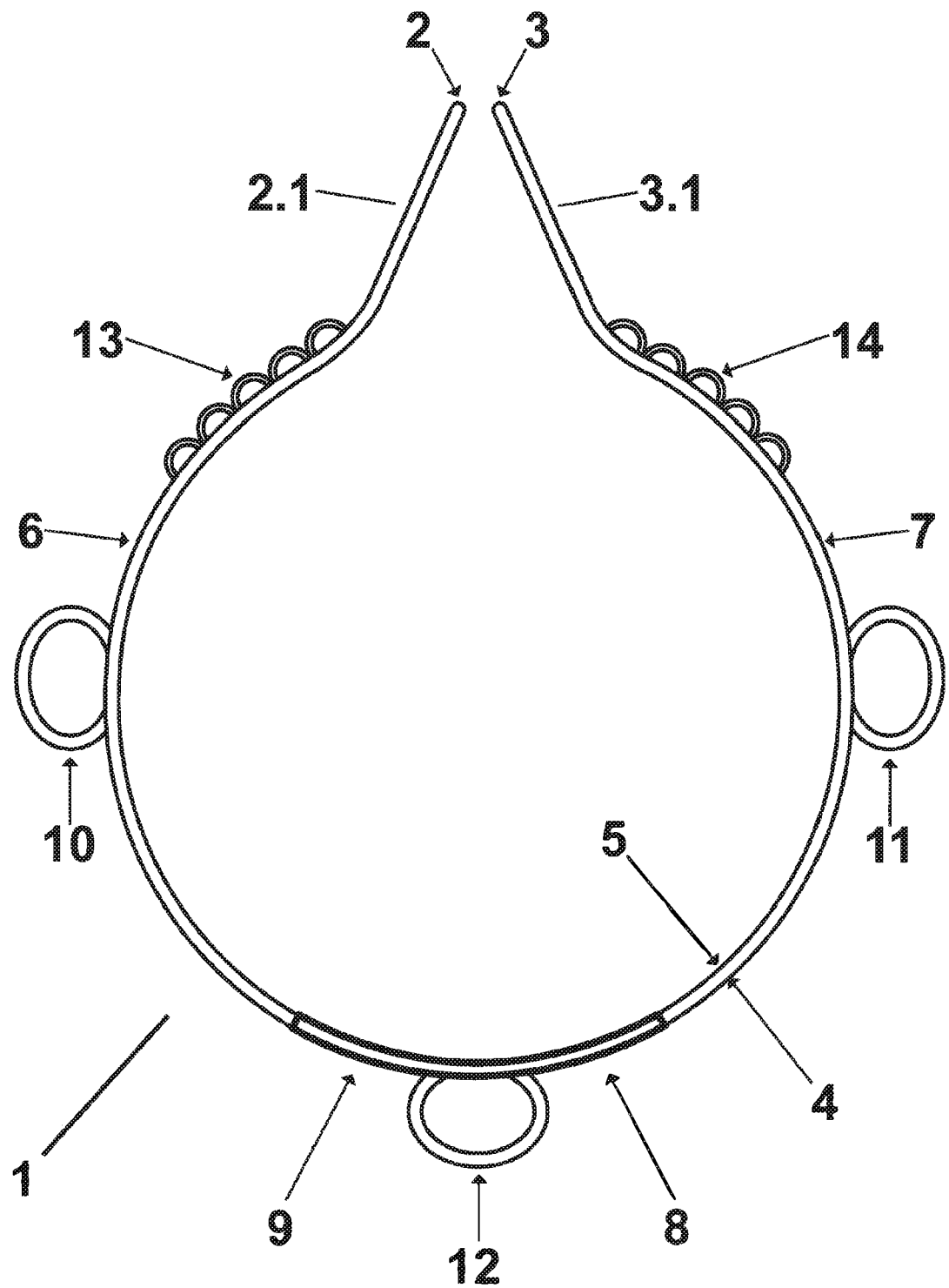
FIG. 1. View of the open ring before positioning. The adjustment loops for tying are appreciated and the ends for tying in the upper part of the figure. The lower part of the figure shows the sleeve or support for the urethra and the gripping rigid loops in positions 3, 6 and 9.
Figure 2:
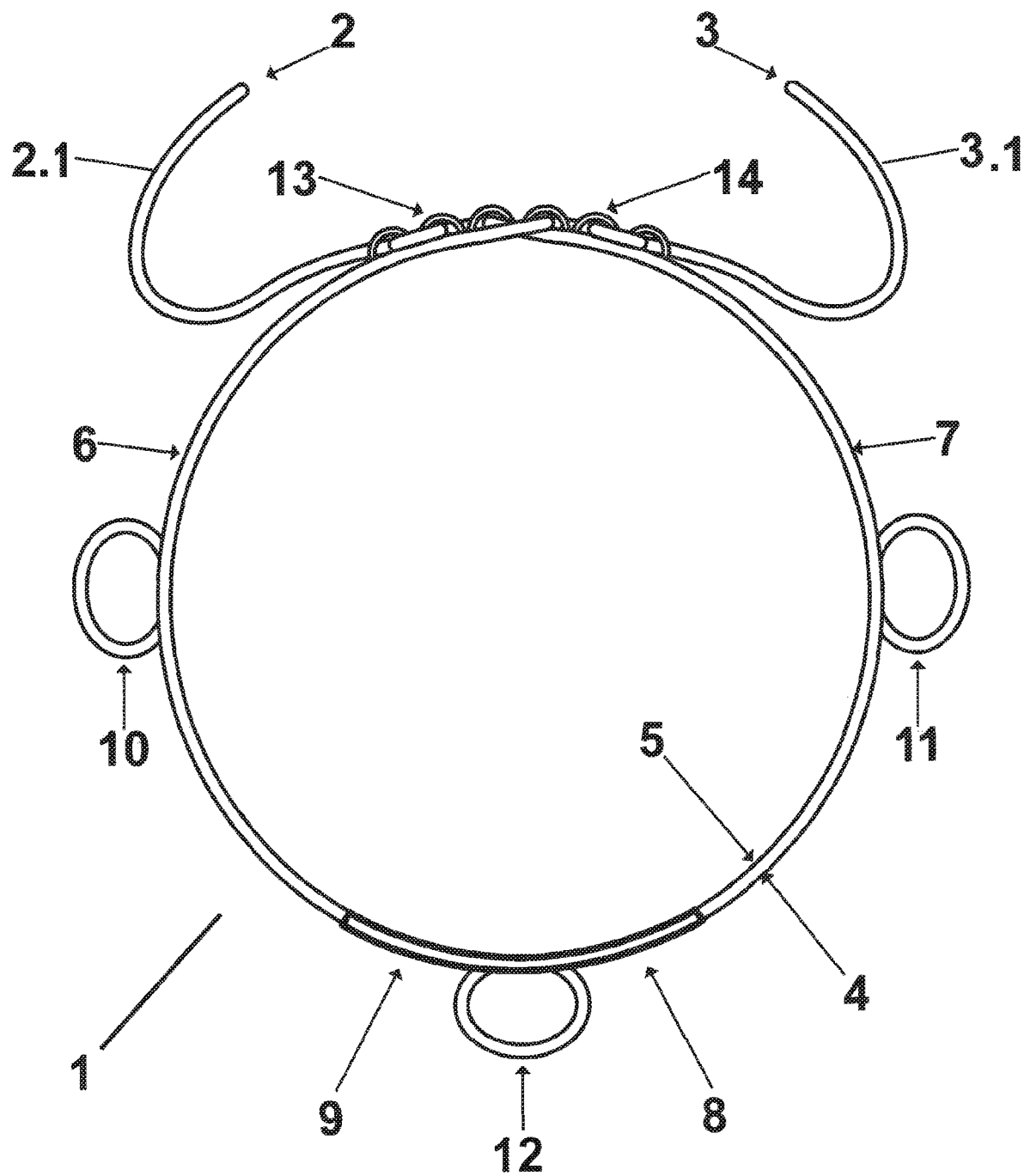
FIG. 2. View of the closed ring. The adjustment loops previously tied and the remaining ends in the upper part of the figure are appreciated. In the lower part of the figure it is visible the sleeve or support for the urethra and the gripping rigid loops in positions 3, 6 and 9.

The constrictor ring of this invention will now be described with reference to a preferred embodiment and the accompanying drawings, wherein the same signs and numbers refer to the same elements.

The constrictor ring of this invention comprises:

An elongated member of circular cross section (1), made of a flexible material, having: a first end (2) and a corresponding first end portion (2.1); a second end (3) and a second corresponding end portion (3.1); an external longitudinal face (4) and an opposite internal longitudinal face (5), oriented in a radical direction towards the center of the ring; wherein each of said end portions (2.1) and (3.1) can be closed by forming a ring having a first side arc portion (6), a second side arc portion (7) and a lower arc portion (8); and in such a way that a first end portion (2.1) is closed on top of the second side arc portion (7) and the second end portion (3.1) is closed on top of the first arc portion of the side arc (6);

a sleeve (9) made of a rigid or semi-rigid material longitudinally covering a central portion of the lower arch portion (8) of the ring, said sleeve having an external longitudinal surface and an opposite internal longitudinal surface oriented in a radial direction towards the center of the ring to protect the urethra when the ring is adjusted;

fastening means comprising: a first gripping loop (10) made of a rigid or semi-rigid material attached to the external longitudinal portion (4) of the first side arch portion (6) in a central portion thereof (a position equivalent to the 9 o'clock in the ring); a second gripping loop (11) made of a rigid or semi-rigid material attached to the external longitudinal portion (4) of the second side-arc portion (7) in a central portion thereof (a position equivalent to the 3 o'clock in the ring); and a third gripping loop (12) made of a rigid or semi-rigid material attached to the external longitudinal portion (4) of the sleeve (9) in a central part thereof (a position equivalent to 6 o'clock in the ring), where said loops are of a size such that they can be pushed by a user's fingers;

releasable securing and adjusting means for securing each end portion in a plurality of positions on the upper portion of a respective side arc portion, wherein said securing means comprise: a first plurality of adjustment loops (13), located longitudinally on the outer face of the upper part of the first side arc portion; and a second plurality of adjustment loops (14) located longitudinally on the outer face of the upper part of the second side arc portion; wherein the first end of the elongated member (2.1) can be held in any loop of the second plurality of loops (14) (passing said end through the respective loop and tying it in said loop and optionally in any other successive loop) and; wherein the second end of the elongated member (3.1) can be held in any loop of the first plurality of loops (13) (passing said end through the respective loop and tying it in said loop and optionally in any other successive loop); and wherein each loop of the first and second plurality of loops corresponds to an adjustment position of a plurality of adjustment positions and constriction levels.

One way to place the constrictor ring of the present invention in the penis, comprises in firstly fitting the ring loosely to be able to slide it in the penis to the base, locating the sleeve (9) in such a way that it is located on the urethra. Once the ring has been placed in the base, the constriction ring can be adjusted by holding the respective ends in any adjustment loop to achieve the desired constriction, subsequently, exert a downward pressure on the loops towards the pubis joint (symphysis pubis) in the precise position where the main venous drainage can be obstructed.

In other embodiments of the invention, the cross section of the ring may have a polygonal shape, and the securing mechanisms may comprise a member in any form in the manner of a handle, such as quadrangular, of any size in any amount (more than two), location or arrangement to facilitate handling and placement of the ring and can even be an integral part of the ring.

Also, the securing and adjusting means may comprise any other alternative means, such as ribbed members with teeth located in the same position as the plurality of adjustment loops, and the plurality of teeth located at each end portion in such a way that said teeth can engage in one of the teeth of a respective grooved member, thus being able to achieve a plurality of adjustment positions.

Likewise, the ring can be made of a semi-rigid material and have adjustment means similar to those of WO1998012986A2 including the respective securing means.

Additionally, the sleeve (9) of rigid material can comprise a section of rigid material that forms an integral part of the ring, forming a rigid portion that could have a different curvature, preferably of smaller diameter, generating a greater curvature and space in a position at six o'clock of the ring.

It should finally be understood that the constrictor ring of the present invention is not limited to the modality described above and that those skilled in the art will be enabled, by the information disclosed herein, to effect changes in the constrictor ring of the present invention, whose scope will be established exclusively by the following claims.

What is claimed is:

1. A constrictor ring for a penis comprising:
    a ring having a first and a second free end superimposed and having an external perimeter face and an internal perimeter face oriented radially towards center of the ring;
    a grip configured to grip and position the ring, comprising two or more gripping members located on the external perimeter face of the ring; and
    an adjuster configured to keep each of the free ends secured in a plurality of adjustment positions representing degrees of constriction,
    wherein the ring further comprises a first side arc portion, a second side arc portion and a lower arc portion, wherein said adjuster is located between the first and second free ends and the first and second side arc portions, and
    wherein the ring further comprises a rigid portion located in the lower arch portion to protect a urethra when the ring is adjusted, wherein the rigid portion is more rigid compared other portions of the ring and comprises a greater curvature compared to other portions of the ring.

2. The constrictor ring for the penis according to claim 1, further comprising a fastener comprising fastening members.

3. The constrictor ring for the penis according to claim 2, wherein the ring further comprises an external longitudinal side and an opposite internal longitudinal face, oriented in a radial direction towards the center of the ring, wherein each of said first and second free end can be closed by forming a ring having the first side arc portion, the second side arc portion and a lower arc portion in such a way that the first free end is closed on an upper part of the second side arc portion and the second free end closed on an upper part of the first side arc portion.

4. The constrictor ring for the penis according to claim 3, comprising an additional sleeve made of a rigid material longitudinally covering a central portion of the lower arch portion of the ring, said sleeve having an external longitudinal surface and an opposite internal longitudinal surface oriented in a radial direction towards the center of the ring to protect the urethra when the ring is adjusted.

5. The constrictor ring for the penis according to claim 3, wherein the fastener further comprises:
    a first loop made of a rigid material attached to an external longitudinal portion of the first side arc portion in a central portion thereof;
    a second loop made of a rigid material attached to an external longitudinal portion of the second side arc portion in central portion thereof; and a third loop made of a rigid material attached to an outer longitudinal surface of a sleeve in a central part thereof, wherein said loops are of a size such that they can be pushed by fingers of a user.

6. The constrictor ring for the penis according to claim 3, wherein the adjuster comprises:

a first plurality of adjustment loops located longitudinally on an outer face of the upper part of the first side arc portion; and a second plurality of adjustment loops located longitudinally on an outer face of the upper part of the second side arc portion, wherein the first free end can be held in any loop of the first plurality of loops, passing said free end through a respective loop and tying it in said loop;

wherein the second free end be held in any loop of the second plurality of loops, passing said free end through a respective loop and tying it in said; and wherein each said loop of the first and second plurality of loops corresponds to an adjustment position of a plurality of adjustment positions and constriction levels.

7. The constrictor ring for the penis according to claim 1, wherein the adjuster comprises a releasable retainer located at each end, in which each end cooperates with a releasable retention mechanism of an opposite side.

* * * * *